United States Patent [19]  [11]  4,299,968
Confalone et al.  [45]  Nov. 10, 1981

[54] NOVEL THIOPHENE COMPOUNDS

[75] Inventors: Pasquale N. Confalone, Bloomfield; Giacomo Pizzolato, Belleville; Milan R. Uskokovic, Upper Montclair, all of N.J.

[73] Assignee: Hoffmann-La Roche Inc., Nutley, N.J.

[21] Appl. No.: 105,804

[22] Filed: Dec. 20, 1979

Related U.S. Application Data

[63] Continuation of Ser. No. 931,238, Aug. 7, 1978, abandoned, which is a continuation of Ser. No. 716,854, Aug. 23, 1976, abandoned, which is a continuation-in-part of Ser. No. 421,460, Dec. 3, 1973, Pat. No. 3,978,084.

[51] Int. Cl.$^3$ .................. C07D 333/24; A61K 31/38
[52] U.S. Cl. ..................................... 549/68; 424/275
[58] Field of Search ......................................... 549/68

[56] References Cited

U.S. PATENT DOCUMENTS

| | | |
|---|---|---|
| 2,443,598 | 6/1948 | Cheney . |
| 2,502,421 | 4/1950 | Cheney . |
| 2,502,423 | 4/1950 | Cheney . |
| 2,502,424 | 4/1950 | Cheney . |
| 3,076,817 | 2/1963 | Fiesselman . |
| 3,445,473 | 5/1969 | Ruschig et al. . |
| 3,795,681 | 3/1974 | Ruschig et al. . |
| 3,823,161 | 7/1974 | Lesser . |
| 3,828,001 | 8/1974 | Brood . |
| 3,855,243 | 12/1974 | Ruschig et al. . |
| 3,929,833 | 12/1975 | Krieger et al. . |
| 3,963,750 | 6/1976 | Goudie . |
| 3,978,084 | 8/1976 | Confalone et al. . |

FOREIGN PATENT DOCUMENTS

| | | |
|---|---|---|
| 574279 | 12/1945 | United Kingdom . |
| 608969 | 9/1948 | United Kingdom . |
| 837086 | 6/1960 | United Kingdom . |
| 1278084 | 6/1972 | United Kingdom . |

OTHER PUBLICATIONS

Baker et al., Jour. Org. Chem., v. 18, pp. 138–152 (1953).

*Primary Examiner*—Alan Siegel
*Attorney, Agent, or Firm*—Jon S. Saxe; Bernard S. Leon; George W. Johnston

[57]  ABSTRACT

Novel thiophene compounds having utility as biotin intermediates and blood lipid lowering agents, as well as related processes and intermediates, are disclosed.

5 Claims, No Drawings

NOVEL THIOPHENE COMPOUNDS

CROSS REFERENCE TO RELATED APPLICATIONS

This is a continuation of U.S. Patent Applicaton Ser. No. 931,238, filed Aug. 7, 1978, now abandoned, which in turn is a continuation of U.S. Patent Application Ser. No. 716,854, filed Aug. 23, 1976, now abandoned, which in turn is a continuation-in-part of U.S. Patent Application Ser. No. 421,460, filed Dec. 3, 1973, now U.S. Pat. No. 3,978,084.

SUMMARY OF THE INVENTION

This invention is directed to novel thiophene compounds of the formula:

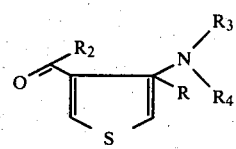

wherein R is aryl, aralkyl, $-(CH_2)_n-R_5$, and

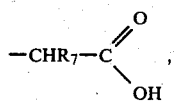

where $R_5$ is hydroxy or

with $R_6$ being hydrogen, hydroxy, lower alkoxy, amino and $R_7$ is lower alkyl, n is an integer from 1-6, $R_2$ is hydrogen, hydroxy, lower alkoxy, or amino; $R_3$ and $R_4$, which may be the same or different, are lower alkyl, aryl, aralkyl, acyl and hydrogen;
and the pharmaceutically acceptable salts thereof.

Compounds within the scope of formula I are useful as intermediates in the synthesis of biotin and as anti-obesity and blood lipid lowering agents.

DETAILED DESCRIPTION OF THE INVENTION

As used throughout this application, the term "lower alkyl" denotes straight and branched chain, saturated aliphatic alkyl groups having from 1 to 8 carbon atoms, such as methyl, ethyl, propyl, isopropyl and the like. The term "lower alkoxy" denotes saturated straight or branched chain alkoxy groups having from 1 to 8 carbon atoms, such as methoxy, ethoxy, propoxy, isopropoxy and the like. The term "halogen" includes all four halogens, i.e., chlorine, bromine, iodine, and fluorine. The term "acyl" refers to acyl groups having attached thereto lower alkyl, aryl, aralkyl, alkoxy, and amino moieties. Typical acyl groups include benzoyl, acetyl, propionyl, carbomethoxy, aminocarbonyl and the like. The term "aryl" denotes mono-nuclear aryl groups such as unsubstituted or substituted phenyl, said substitutions being in one or more positions and selected from lower alkyl, trihalomethyl, such as trifluoro and trichloro methyl, aralkyl, halogen, lower alkoxy, amino, nitro, mono and di-lower alkylamino. The term "amino" as used herein includes unsubstituted and substituted amino groups wherein said substituents may be lower alkyl, acyl, aryl or aralkyl. The term "alkali metal" denotes metals such as sodium, potassium, lithium and the like. The term "alkanol" as used herein, denotes straight or branched chain alcohols having 1-20 carbon atoms. The term "lower alkanols" denotes alkanols having 1-6 carbon atoms. The term "alkoxide" as used herein, refers to metal salts, preferably alkali and alkaline earth metal salts of alkanols. The term "alkaline earth metal" refers to calcium, barium, magnesium and the like. The term "lower alkanoic acids" denotes alkanoic acids having from 1-8 carbon atoms.

In accordance with this invention, the thiophene of formula I is obtained by initially reacting a compound of the formula:

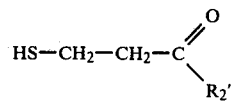

with a compound of the formula:

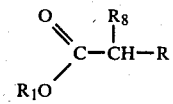

to form a compound of the formula:

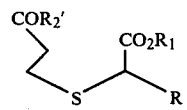

wherein R is as previously defined, $R_1$ is lower alkyl, $R_2'$ is lower alkoxy and $R_8$ is halogen, mesyloxy and tosyloxy.

The foregoing reaction is carried out in the presence of a lower alkanol and an alkali metal alkoxide, preferably methanol and sodium methoxide. Although temperature and pressure are not critical, this reaction is generally carried out at atmospheric pressure and temperatures of from about 15° C. to about 60° C., preferably 25° C.

Compound IV is then treated with an alkali metal alkoxide, preferably sodium methoxide in the presence of an aromatic hydrocarbon, preferably benzene to form a compound of the formula:

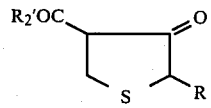

wherein R and $R_2'$ are as defined above. Although temperatures and pressures are not critical, this reaction is generally carried out at atmospheric pressure and a temperature of from about 15° C. to about 60° C., preferably 25° C.

Compound V is then transformed to an oxime of the formula:

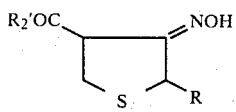

wherein R and R₂' are as defined above.

Any conventional method of preparing an oxime from a keto compound can be used to convert the 4,5-dihydrothiophene of formula V to the oxime of formula VI. Preferably, the 4,5-dihydrothiophene of formula V is treated with a hydroxylamine hydrohalide, preferably hydroxylamine hydrochloride, in a nitrogen-containing base. In carrying out this reaction, any conventional nitrogen-containing base can be utilized. The preferred nitrogen-containing bases are the amines. Among the amines which can be utilized are the primary amines, such as the loweralkylamines, particularly methylamine, ethylamine, and aniline; the secondary amines, such as the diloweralkylamines, particularly dimethylamine and diethylamine, and pyrrole; and the tertiary amines, such as the triloweralkylamines, particularly trimethylamine and triethylamine, pyridine and picoline. Also, in carrying out this reaction with a hydroxylamine hydrohalide, temperature and pressure are not critical, and the reaction can be suitably carried out at from room temperature to reflux and at atmospheric pressure. Preferably, this reaction is carried out at room temperature (about 22° C.). Further, this reaction can be carried out in an inert organic solvent. In this reaction any conventional inert organic solvent can be utilized, such as the aliphatic or aromatic hydrocarbons, as for example n-hexane or benzene. Preferably, this reaction is carried out in an excess of the nitrogen-containing base, which serves as the solvent medium.

The oxime of formula VI is converted to an amine of the formula:

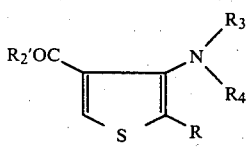

wherein R and R₂' are as above, R₃ and R₄ are hydrogen. This reaction is suitably carried out by treating the oxime of formula VI with an acid, preferably a hydrohalide, in an inert, solvent. This reaction can be carried out preferably by treating the oxime of formula VI with hydrogen chloride. In carrying out this reaction, any conventional inert solvent can be utilized. Preferred inert organic solvents are the ethers, particularly the dilower alkyl ethers, such as diethyl ether, and the cyclic ethers, such as tetrahydrofuran and dioxane. Other solvents that may be employed are lower alkanols and water. In carrying out this reaction, temperature and pressure are not critical, and this reaction can be suitably carried out at from 0° C. to about 70° C. and at atmospheric pressure. Preferably, this reaction is carried out at room temperature. Where it is desired that R₃ and/or R₄ be lower alkyl or lower acyl, these moieties may be introduced by conventional procedures for converting an aromatic primary amine to N-alkyl and N-acyl derivatives. Compound VII may be transformed to the corresponding aldehyde, acid, amides, or other esters by conventional methods for converting esters to the aforementioned compounds.

Compound VII, where R₂' is lower alkoxy, may then be converted to a compound of the formula:

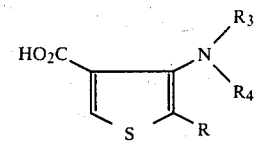

wherein R, R₃ and R₄ are as previously defined.

In carrying out this reaction, any conventional method of basic hydrolysis can be utilized. This hydrolysis can be suitably carried out in a conventional inert organic solvent. The preferred solvents are the lower alkanols, particularly methanol and ethanol, and the aqueous ether solvents, preferably the aqueous dilower alkyl ethers, particularly diethyl ether, and the aqueous cyclic ethers, particularly tetrahydrofuran and dioxane. In this reaction, any conventional base can be utilized. Among the preferred bases are the alkali metal hydroxides, such as sodium, potassium and lithium hydroxide, and the alkaline earth metal hydroxides, such as barium, calcium and magnesium hydroxide, especially the alkali metal hydroxides. In this hydrolysis, temperature and pressure are not critical, and this reaction can be suitably carried out at from about 0° C. to about 100° C. and at atmospheric pressure. Preferably, this reaction is carried out at reflux, especially at about 70° C.

The compounds of formula I, particularly where R is

where n is 4 or the corresponding lower alkyl esters are disclosed in application Ser. No. 421,460, filed Dec. 3, 1973 as intermediates in the synthesis of biotin, said disclosure being incorporated herein by reference.

The following non-limiting examples further illustrate this invention. All temperatures are in degrees Centigrade and the ether used is diethyl ether.

EXAMPLE 1

A solution of 104.95 g. (0.873 mole) of methyl-3-mercaptopropionate in 200 ml. methanol was cooled to 0° and treated with 207.5 g. of a 25% solution of sodium methoxide in methanol. To the resulting homogeneous solution was added dropwise under argon 200.0 g. (0.873 mole) of methyl-α-bromophenyl acetate in 200 ml. methanol. The reaction was stirred at 25° overnight. The solvent was removed by evaporation, and the residue was partitioned between water and methylene chloride to afford 234.0 g. (100%) of 2-phenyl-3-thia-adipic acid dimethyl ester as a colorless oil.

EXAMPLE 2

A solution of 234.0 g. (0.873 mole) of 2-phenyl-3-thia-adipic acid dimethyl ester in 300 ml dry benzene was added dropwise at 25° to 54.05 g. (0.873 mole) of sodium methoxide. The reaction was stirred overnight and poured into water. The solid was filtered off and the filtrate was extracted two times with ether. The solid was then added to aqueous phase which was then acidified to pH 1 with 6 N HCl. The mixture was extracted three times with methylene chloride. The organic extracts were dried over sodium sulfate and evaporated to afford 145.24 g. (0.615 mole, 71%) of 4-carbomethoxy-3-keto-2-phenyltetrahydrothiophene as a pale yellow oil.

EXAMPLE 3

A solution of 82.24 g. (0.348 mole) of 4-carbomethoxy-3-keto-2-phenyltetrahydrothiophene in 120 ml. anhydrous pyridine was treated with 28.85 g. (0.418 mole) of hydroxylamine hydrochloride. The solution was stirred at 25° for two days, and the solvent was evaporated in vacuo. The residue was partitioned between 1 N HCl and methylene chloride. The aqueous phase was further extracted with methylene chloride. The organic extracts were pooled, dried over sodium sulfate, and evaporated to give 90.0 g. (0.319 mole, 92%) of 4-carbomethoxy-3-keto-2-phenyltetrahydrothiophene oxime as a colorless oil.

EXAMPLE 4

Into a solution of 80.0 g. (0.319 mole) of 4-carbomethoxy-3-keto-2-phenyltetrahydrothiophene oxime in 600 ml. of anhydrous ether was bubbled gaseous hydrogen chloride at 0° for one hour. The suspension was treated with 300 ml. of methanol and stirred at 25° overnight. The product was collected by filtration and washed with ether to yield 70.0 g. of 4-amino-5-phenylthiophene-3-carboxylic acid methyl ester hydrochloride as a pale yellow solid, m.p. 181°-182°. The compound may be recrystallized from methanol.

EXAMPLE 5

A solution of 10.0 g. (0.0371 mole) of 4-amino-5-phenylthiophene-3-carboxylic acid methyl ester hydrochloride in 80 ml. methanol was treated with 82 ml. of 1 N sodium hydrochloride (0.0816 mole). The reactants were heated under reflux for 30.0 minutes, and cooled to room temperature. The pH was adjusted to 5 and the product which separated was filtered off and dried to afford 8.2 g. (100%) of pure 4-amino-5-phenylthiophene-3-carboxylic acid, m.p. 201°-202° after recrystallization from ethylacetate/pentane.

EXAMPLE 6

A solution of 13.3 g. (0.0493 mole) of 4-amino-5-phenylthiophene-3-carboxylic acid methyl ester hydrochloride in 70 ml. of anhydrous pyridine was treated with 5.93 ml (0.0628 mole) acetic anhydride and heated at 50° for 4.0 hours. At this point, an additional 5 ml. acetic anhydride was added and the solution was heated at 50° for a further 16.0 hours. The reaction was cooled, and the solvent was evaporated. The residue was partitioned between 1 N HCl and methylene chloride. The aqueous phase was further extracted with methylene chloride. The organic extracts were combined, dried over sodium sulfate, and evaporated to yield 13.7 g. (0.49 mole, 100%) of pure 4-acetamido-5-phenylthiophene-3-carboxylic acid methyl ester. The compound was recrystallized from ethylacetate/pentane to yield white needles, m.p. 117°-118°.

EXAMPLE 7

A solution of 8.6 g. (0.0313 mole) of 4-acetamido-5-phenylthiophene-3-carboxylic acid methyl ester in 30 ml. methanol was treated with 34.4 ml. 1 N NaOH and heated under reflux for 1.5 hours. The reaction was cooled, acidified with 1 N HCl and extracted with methylene chloride/methanol, 8:2. The organic extracts were pooled, dried over sodium sulfate and evaporated to yield 7.2 g. (88%) of pure 4-acetamido-5-phenylthiophene-3-carboxylic acid, m.p. 182°-183°, after recrystallization from ethyl acetate.

EXAMPLE 8

Into a solution of 110 g. (0.381 mole) of 4-carbomethoxy-2-(4,5-dihydrothiophen-3(2H)-one)valeric acid methyl ester oxime in 1500 ml. anhydrous diethyl ether, submerged in an ice bath, was bubbled hydrogen chloride gas. After ¾ hr., the flask containing the reaction mixture was stoppered and the reaction allowed to proceed at 25° C. for 24 hrs. The reaction mixture was concentrated on a rotary evaporator, and the residue was taken up in 500 ml. water and made basic by the addition of 1000 ml. 10% by weight aqueous sodium bicarbonate solution. The reaction mixture was then extracted three times with 500 ml. portions of dichloromethane. The organic phases were dried over anhydrous sodium sulfate and evaporated to afford 90.0 g. (0.316 mole, 83%) of 3-amino-4-carbomethoxy-2-thiophenevaleric acid methyl ester as a pale yellow crystalline solid; m.p. 50°-52°. The aqueous phase was acidified with 6 N hydrochloric acid to pH 4 and extracted three times with 300 ml. portions of dichloromethane. The organic phase was dried over anhydrous sodium sulfate and evaporated to afford 13.0 g. (0.048 mole, 13%) of 3-amino-4-carbomethoxy-2-thiophenevaleric acid as a white solid; m.p. 130°-132°. An analytical sample was obtained by recrystallization from ethyl acetate; m.p. 131°-132°.

EXAMPLE 9

A solution of 18.64 g (0.0687 mole) of 3-amino-4-carbomethoxy-2-thiophenevaleric acid methyl ester in 400 ml. of methanol was treated with 185 ml. (0.185 mole) of 1 N sodium hydroxide. The reaction mixture was refluxed for one hour, cooled, and concentrated. The residue, consisting essentially of 3-amino-4-carbomethoxy-2-thiophenevaleric acid, was acidified to pH 1 with 50 ml. 6 N hydrochloric acid and evaporated to dryness leaving 16.64 g. (0.0685 mole, 100% of 3-amino-4-carboxy-2-thiophenevaleric acid hydrochloride as a white solid, admixed with 7.0 g of the sodium chloride by-product. Purification was achieved by extraction with hot ethanol. The product was recrystallized from methanol/diethyl ether to afford pure product, m.p. 186°(dec.).

The following examples, 10–21, illustrate pharmaceutical formulations containing compounds having anti-obesity and lipid lowering properties and methods of preparing these formulations.

EXAMPLE 10

Tablet Formulation

| Ingredients | mg/tablet | |
|---|---|---|
| | 250 | 500 |
| 4-Amino-5-phenylthiophen-3-carboxylic methyl ester hydrochloride | 250 | 500 |
| Pregelatinized starch | 12.5 | 25 |
| Modified starch | 12.5 | 25 |
| Magnesium stearate | 1.5 | 3 |
| Tablet weight | 276.5 mg | 553 mg |

PROCESS:

1. Mix compound and both starches, mill and remix well.
2. Granulate with water.
3. Dry overnight.
4. Mill with magnesium stearate and remix.
5. Compress on a suitable punch.

EXAMPLE 11

Capsule Formulation

| Ingredients | mg/capsule | |
|---|---|---|
| | 250 | 500 |
| 4-Amino-5-phenylthiophen-3-carboxylic methyl ester hydrochloride | 250 | 500 |
| Cornstarch | 25 | 50 |
| Talc | 4 | 8 |
| Magnesium stearate | 1 | 2 |
| Capsule weight | 280 mg | 560 mg |

PROCESS
1. Mix compound and both starches, mill and remix well.
2. Add talc and magnesium stearate and mix for 5 minutes.
3. Encapsulate in hard-shell capsules.

EXAMPLE 12

Tablet Formulation

| Ingredients | mg/tablet | |
|---|---|---|
| | 250 | 500 |
| 3-Amino-4-carbomethoxy-2-thiophene valeric acid | 250 | 500 |
| Pregelatinized starch | 12.5 | 25 |
| Modified starch | 12.5 | 25 |
| Magnesium stearate | 1.5 | 3 |
| Tablet weight | 276.5 mg | 553 mg |

PROCESS
1. Mix compound and both starches, mill and remix well.
2. Granulate with water.
3. Dry overnight.
4. Mill with magnesium stearate and remix.
5. Compress on a suitable punch.

EXAMPLE 13

Capsule Formulation

| Ingredients | mg/capsule | |
|---|---|---|
| | 250 | 500 |
| 3-Amino-4-carbomethoxy-2-thiophene valeric acid | 250 | 500 |
| Cornstarch | 25 | 50 |
| Talc | 4 | 8 |
| Magnesium stearate | 1 | 2 |
| Capsule weight | 280 mg | 560 mg |

PROCESS
1. Mix compound and both starches, mill and remix well.
2. Add talc and magnesium stearate and mix for 5 minutes.
3. Encapsulate in hard-shell capsule.

EXAMPLE 14

Tablet Formulation

| Ingredients | mg/tablet | |
|---|---|---|
| | 250 | 500 |
| 3-Amino-4-carbomethoxy-2-thiophene methyl ester | 250 | 500 |
| Pregelatinized starch | 12.5 | 25 |
| Modified starch | 12.5 | 25 |
| Magnesium stearate | 1.5 | 3 |
| Total weight | 276.5 mg | 553 mg |

PROCESS
1. Mix compound and both starches, mill and remix well.
2. Granulate with water.
3. Dry overnight.
4. Mill with magnesium stearate and remix.
5. Compress on a suitable punch.

EXAMPLE 15

Capsule Formulation

| Ingredients | mg/capsule | |
|---|---|---|
| | 250 | 500 |
| 3-Amino-4-carbomethoxy-2-thiophene methyl ester | 250 | 500 |
| Cornstarch | 25 | 50 |
| Talc | 4 | 8 |
| Magnesium stearate | 1 | 2 |
| Capsule weight | 280 mg | 560 mg |

PROCESS
1. Mix compound and both starches, mill and remix well.
2. Add talc and magnesium stearate and mix for 5 minutes.
3. Encapsulate in hard-shell capsules.

EXAMPLE 16

Tablet Formulation

| Ingredients | mg/tablet | |
|---|---|---|
| | 250 | 500 |
| 4-Amino-5-phenylthiophen-3-carboxylic acid | 250 | 500 |
| Pregelatinized starch | 12.5 | 25 |
| Modified starch | 12.5 | 25 |
| Magnesium stearate | 1.5 | 3 |
| Tablet weight | 276.5 mg | 553 mg |

PROCESS
1. Mix compound and both starches, mill and remix well.
2. Granulate with water.
3. Dry overnight.
4. Mill with magnesium stearate and remix.
5. Compress on a suitable punch.

EXAMPLE 17

Capsule Formulation

| Ingredients | mg/capsule | |
|---|---|---|
| | 250 | 500 |
| 4-Amino-5-phenylthiophen-3-carboxylic acid | 250 | 500 |
| Cornstarch | 25 | 50 |
| Talc | 4 | 8 |
| Magnesium stearate | 1 | 2 |
| Capsule weight | 280 mg | 560 mg |

PROCESS
1. Mix the compound with the cornstarch, mill and remix well.
2. Add talc and magnesium stearate and mix for 5 minutes.
3. Encapsulate in hard-shell capsules.

EXAMPLE 18

Tablet Formulation

| Ingredients | mg/tablet | |
|---|---|---|
| | 250 | 500 |
| 4-Acetamido-5-phenylthiophen-3-carboxylic acid | 250 | 500 |
| Pregelatinized starch | 12.5 | 25 |
| Modified starch | 12.5 | 25 |
| Magnesium stearate | 1.5 | 3 |
| Tablet weight | 276.5 mg | 553 mg |

PROCESS
1. Mix compound and both starches, mill and remix well.
2. Granulate with water.
3. Dry overnight.
4. Mill with magnesium stearate and remix.
5. Compress on a suitable punch.

EXAMPLE 19

Capsule Formulation

| Ingredients | mg/tablet | |
|---|---|---|
| | 250 | 500 |
| 4-Acetamido-5-phenylthiophen-3-carboxylic acid | 250 | 500 |
| Cornstarch | 25 | 50 |
| Talc | 4 | 8 |
| Magnesium stearate | 1 | 2 |
| Capsule weight | 280 mg | 560 mg |

PROCESS
1. Mix compound with the cornstarch, mill and remix well.
2. Add talc and magnesium stearate and mix for 5 minutes.
3. Encapsulate in hard-shell capsules.

EXAMPLE 20

Tablet Formulation

| Ingredients | mg/tablet | |
|---|---|---|
| | 250 | 500 |
| 4-Acetamido-5-phenylthiophen-3-methyl ester | 250 | 500 |
| Pregelatinized starch | 12.5 | 25 |
| Modified starch | 12.5 | 25 |
| Magnesium stearate | 1.5 | 3 |
| Tablet weight | 276.5 mg | 553 mg |

PROCESS
1. Mix compound and both starches, mill and remix well.
2. Granulate with water.
3. Dry overnight.
4. Mill with magnesium stearate and remix.
5. Compress on a suitable punch.

EXAMPLE 21

Capsule Formulation

| Ingredients | mg/capsule | |
|---|---|---|
| | 250 | 500 |
| 4-Acetamido-5-phenylthiophen-3-methyl ester | 250 | 500 |
| Cornstarch | 25 | 50 |
| Talc | 4 | 8 |
| Magnesium stearate | 1 | 2 |
| Capsule weight | 280 mg | 560 mg |

PROCESS
1. Mix the compound with the cornstarch, mill and remix well.
2. Add talc and magnesium stearate and mix for 5 minutes.
3. Encapsulate in hard-shell capsules.

We claim:

1. A compound of the formula:

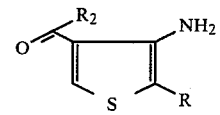

wherein R is aryl and $R_2$ is hydrogen, hydroxy, lower alkoxy or amino,
or pharmaceutically acceptable salts thereof.

2. The compound of claim 1 wherein R is phenyl or phenylsubstituted in one or more positions with lower alkyl, trihalomethyl, halogen, lower alkoxy, amino, nitro, mono(lower alkyl)amino or di(lower alkyl)amino.

3. The compound of claim 2 wherein R is phenyl.

4. The compound of claim 1 wherein said compound is:

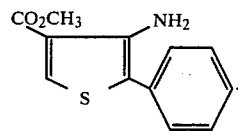

5. The compound of claim 1 wherein said compunds is:

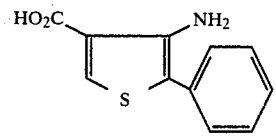

* * * * *